United States Patent

Papantoniou et al.

[11] 3,937,811
[45] Feb. 10, 1976

[54] FATTY COMPOSITIONS FOR USE IN COSMETIC MAKEUP COMPOSITIONS AND SAID COSMETIC MAKEUP COMPOSITIONS

[75] Inventors: Christos Papantoniou, Epinay-sur-Seine; Jean Boulogne, L'Hay-les-Roses, both of France

[73] Assignee: Societe Anonyme dite: L'Oreal, Paris, France

[22] Filed: June 7, 1974

[21] Appl. No.: 477,515

[30] Foreign Application Priority Data
June 8, 1973    Luxemburg............................ 67772

[52] U.S. Cl. ................ 424/64; 252/312; 252/316; 260/18 R; 260/28.5 AV; 260/29.65; 260/29.6 T; 260/37 NP; 260/37 P; 260/80.3 R; 260/80.3 F; 260/80.76; 260/80.81; 424/DIG. 5; 424/59; 424/63; 424/70; 424/78; 424/168; 424/172; 424/357; 424/362; 424/363; 424/365

[51] Int. Cl.²........................................ A61K 7/025

[58] Field of Search .......... 424/63, 64, 70, 78, 365; 424/DIG. 5; 252/312, 316; 260/18 R, 37 NP, 37 P

[56] References Cited
UNITED STATES PATENTS

| | | | |
|---|---|---|---|
| 3,055,297 | 9/1962 | Leeds............................... | 424/78 X |
| 3,088,876 | 5/1963 | Buth .................................... | 424/64 |
| 3,148,125 | 9/1964 | Strianse et al. ....................... | 424/64 |
| 3,321,408 | 5/1967 | Briggs............................. | 424/365 X |
| 3,406,238 | 10/1968 | Freyermuth et al. ............. | 424/63 X |
| 3,489,690 | 1/1970 | Lachampt et al................. | 424/63 X |
| 3,574,822 | 4/1971 | Shepherd et al.................. | 424/63 X |
| 3,639,572 | 2/1972 | Heinrich et al....................... | 424/63 |
| 3,708,435 | 1/1973 | Starkman........................... | 424/64 X |

*Primary Examiner*—Albert T. Meyers
*Assistant Examiner*—Vera C. Clarke
*Attorney, Agent, or Firm*—Cushman, Darby & Cushman

[57] ABSTRACT

A fatty composition for use in producing cosmetic compositions comprising a mixture of at least one cosmetic fatty body and at least one non-toxic copolymer of the formula:

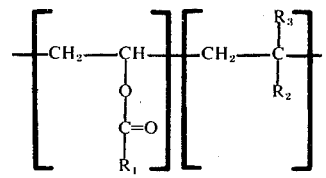

wherein $R_1$ represents a saturated hydrocarbon chain, linear or branched, having from 1-19 carbon atoms;

$R_2$ represents a member selected from the group consisting of a.

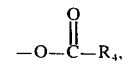

wherein $R_4$ has the same meaning as $R_1$ but is different from $R_1$ in the same copolymer, b. $-CH_2-R_5$, wherein $R_5$ represents a saturated hydrocarbon chain, linear or branched, having from 5-25 carbon atoms, c. $-O-R_6$, wherein $R_6$ is a saturated hydrocarbon chain having from 2 to 18 carbon atoms, and d.

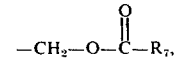

wherein $R_7$ is a saturated hydrocarbon chain, linear or branched, having from 1-19 carbon atoms, and $R_3$ represents hydrogen when $R_2$ represents (a), (b), or (c) or $R_3$ represents methyl when $R_2$ represents (d). The copolymer must contain at least 15 weight percent of at least one monomer of unit Ia or of unit Ib in which the saturated hydrocarbon chain, linear or branched, has at least 7 carbon atoms.

This fatty composition is employed to produce a cosmetic makeup composition, such as lip rouge, in paste or stick form, or mascara, and is present in said cosmetic composition in amounts of 99.5-15 percent by weight of the total weight of the cosmetic composition.

16 Claims, No Drawings

FATTY COMPOSITIONS FOR USE IN COSMETIC MAKEUP COMPOSITIONS AND SAID COSMETIC MAKEUP COMPOSITIONS

The present invention relates to a new fatty composition usefully employed in the production of cosmetic products and especially for makeup products such as lip rouge in stick or paste form and mascara. The present invention relates to cosmetic compositions containing said fatty composition.

As is well known cosmetic compositions of the type as lip rouge in stick or paste form, or mascara, are constituted principally by a fatty base which is a mixture of one or more waxes and one or more oils.

The oils and the waxes which can be used for the production of such makeup composition are diverse, their choice depending principally on the ultimate use of the compositions.

Up to now, one has exclusively visualized the use of certain waxes or oils of animal, vegetable or mineral origin, or of certain synthetic substances having properties analogous to those of natural substances and thus being able to advantageously replace them.

Although utilized currently in cosmetics, these waxes and oils, which are of natural or synthetic origin, do not permit to confer to lip rouges in stick or in paste form or to mascara totally satisfactory characteristics notably in that which concerns on the one hand the firmness of the sticks and on the other hand the brightness, the improved adherence and the persistence of the film deposited on the lips or on the eyebrows.

In effect it is necessary on the one hand that lip rouge in the form of a stick exhibits good firmness so that during application it does not break or fracture and on the other hand that lip rouge in the form of the paste and mascara exhibit good adherence while having sufficient brightness.

The applicants, after considerable research, have surprisingly found that it was possible to produce excellent makeup products and notably lip rouge in stick or in paste form, as well as mascara, having the different characteristics mentioned above when there is used as the fatty base a composition containing in admixture at least one cosmetic fatty body and at least one copolymer of a particular type having great affinity for the fatty body and being non-toxic.

The present invention has then for an object a new fatty composition for use in the production of cosmetic products, this new fatty composition being characterized by the fact that it comprises in admixture at least one cosmetic fatty body and at least one non-toxic copolymer having the following formula:

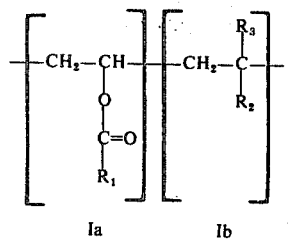

wherein $R_1$ represents a saturated hydrocarbon chain, linear or branched, having from 1 to 19 carbon atoms; $R_2$ represents a member selected from the group consisting of a. 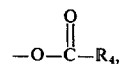

wherein $R_4$ has the same meaning as $R_1$ but is different from $R_1$ in the same copolymer, b. $-CH_2-R_5$, wherein $R_5$ represents a saturated hydrocarbon chain, branched or linear, having from 5 to 25 carbon atoms, c. $-O-R_6$, wherein $R_6$ represents a saturated hydrocarbon chain having from 2 to 18 carbon atoms, and d. 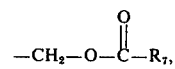

wherein $R_7$ represents a saturated hydrocarbon chain, linear or branched, having from 1 to 19 carbon atoms and $R_3$ represents hydrogen when $R_2$ represents radicals (a), (b) or (c) or $R_3$ represents methyl when $R_2$ represents radical (d), the said copolymer being able to be constituted by at least 15% by weight of at least one monomer derived from a unit Ia or from a unit Ib in which the hydrocarbon chains, saturated or branched, have at least 7 carbon atoms.

According to the invention, the term "fatty body" means a wax or a mixture of waxes or even a mixture of at least one wax and at least one oil. Preferably, the fatty body according to the invention is constituted by from 6 to 100% of at least one wax and from 0 to 94% of at least one oil.

The presence in the fatty composition of at least one copolymer such as defined above permits to impart to makeup products present in the form of the stick a great resistance to breaking, excellent brightness and good holding power for the film deposited on the lips.

For the compositions present in the form of a paste, and notably lip rouges or lip polishes, the presence of at least one copolymer imparts to these compositions very good unctuousness, great flexibility and excellent brightness of the film deposited on the lips as well as good adherence and improvement in the holding power of the brightness of the film.

For compositions present in the form of mascara, the presence of a copolymer also improves the adherence of the film and increases the resistance to water of the film deposited on the eyelashes.

Copolymers such as described above exhibit the characteristic of being fat soluble, that is, they have a great affinity for the waxes and the oils with which they are admixed. It is this important property which achieves the excellent qualities of the cosmetic compositions produced with the fatty composition of the present invention.

This fat solubility of the copolymers is due to the presence of at least 15% by weight of at least one monomer carrying a fatty chain having from 7 to 25 carbon atoms.

According to the invention, the fatty body is present in an amount between about 65 to 98%, preferably between 75 to 95%, and the copolymer is present in amounts between 2 to 35%, preferably 5 to 25% relative to the total weight of the fatty composition.

It must be remarked that in the fatty composition according to the invention, the copolymer such as defined above can be used alone or in admixture with another copolymer of the same type or even in admixture with a fat soluble homopolymer.

Representative of such homopolymers are those resulting from the homopolymerization of vinyl esters having from 9 to 22 carbon atoms or of alkyl acrylates or alkyl methacrylates, the alkyl radicals having from 10 to 20 carbon atoms.

Preferably the homopolymer is selected from the group consisting of polyvinyl stearate, polyvinyl stearate crosslinked with the aid of divinylbenzene, diallylether or diallyl phthalate, polystearylmethacrylate, polyvinylaurate, polylaurylmethacrylate, polystearylacrylate, polylaurylacrylate, these polyacrylates and polymethacrylates being able to be cross-linked with the aid of ethylene glycol dimethacrylate or tetraethylene glycol dimethacrylate.

As has been stated above, the fatty body can be constituted by one or more waxes and in this case, they can be for example ozokerite, lanolin, lanolin alcohol, hydrogenated lanolin, acetylated lanolin, lanolin wax, beeswax, Candellila wax, microcrystalline wax, Carnauba wax, cetyl alcohol, stearyl alcohol, spermaceti, cocoa butter, fatty acids of lanolin, petrolatum, Vaseline, mono-, di- and triglycerides which are solid at 25°C, fatty esters which are solid at 25°C, silicone waxes such as methyloctadecane-oxypolysiloxane and poly (dimethylsiloxy) stearoxysiloxane, stearyl monoethanolamide, rosin and its derivatives such as the abietates of glycol and glycerol, hydrogenated oils solid at 25°C, sucroglycerides, and the oleates, myristates, lanolates, stearates and dihydroxystearates of Ca, Mg, Zr and Al.

The fatty body can also be constituted by a mixture of at least one wax and at least one oil and in this case the oil can be for example, paraffin oil, Purcellin oil, perhydrosqualene, sweet almond oil, avocado oil, calophyllum oil, ricin oil, horse oil, hog oil, olive oil, mineral oil having a boiling point between 310° and 410°C, silicone oil such as dimethylpolysiloxane, linoleic alcohol, linolenic alcohol, oleyl alcohol, the oil of cereal germs as the oil of wheat germ, isopropyl lanolate, isopropyl palmitate, isopropyl myristate, butyl myristate, cetyl myristate, hexadecyl stearate, butyl stearate, decyl oleate, acetyl glycerides, the octanoates and decanoates of alcohols and polyalcohols such as those of glycol and glycerol, ricin oleates of alcohol and polyalcohols such as those of cetyl, isostearyl alcohol, isocetyl lanolate, isopropyl adipate, hexyl laurate and octyl dodecanol.

As can be seen from formula I, the copolymers included in the fatty composition result from the copolymerization of at least one vinyl ester and at least one other monomer which can be an α-olefin, an alkylvinylether or an allyl or methallyl ester.

The α-olefins, the alkylvinylethers and the allyl or methallyl esters not being homopolymerizable monomers as opposed to vinyl esters, it follows that the copolymers which result from the copolymerization of at least one vinyl ester and at least one non-homopolymerizable monomer such as those mentioned above, are in general constituted by 50 to 95 molar percent of at least one unit Ia and from 50 to 5 molar percent of at least one unit Ib, wherein $R_2$ represents the radicals $-CH_2-R_5$, $-O-R_6$ or

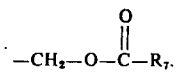

The copolymers can also result from the copolymerization of at least one vinyl ester and at least one other vinyl ester different from the first.

In this case, as indicated above, the vinyl esters are homopolymerizable and the copolymers of this type are generally constituted by 10 to 90 molar percent of at least one unit Ia and from 90 to 10 molar percent of at least one unit Ib wherein $R_2$ represents the radical

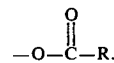

Representative vinyl esters leading to unit of formula Ia, or to the unit of formula Ib in which $R_2 =$

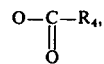

include vinyl acetate, vinyl propionate, vinyl butanoate, vinyl octanoate, vinyl decanoate, vinyl laurate, vinyl stearate, vinyl isostearate, vinyl-2,2-dimethyloctanoate, vinyl dimethylpropionate, and vinyl cecanoate.

Representative α-olefins leading to the unit of formula Ib wherein $R_2 = CH_2-R_5$, include 1-octene, 1-dodecene, 1-octadecene, 1-eicosene, and mixtures of α-olefins having from 22 to 28 carbon atoms.

Representative alkylvinylethers leading to the unit of formula Ib wherein $R_2 = -O-R_6$, including ethylvinylether, n-butylvinylether, isobutylvinylether, decylvinylether, dodecylvinylether, cetylvinylether and octadecylvinylether.

Representative allyl or methallyl esters leading to the unit of formula Ib wherein $R_2 =$

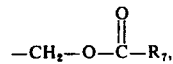

include allyl and methallyl acetates, propionates, dimethylpropionates, butyrates, hexanoates, octanoates, decanoates, laurates, 2,2-dimethylpentanoates, stearates and eicosanoates.

The copolymers such as have been described above can also be crosslinked with the aid of certain types of crosslinking agents which have for their purpose the sensible increase in their molecular weight.

This cross-linking is effected during the copolymerization and the cross-linking agents can be either of the vinyl type or the allyl or methallyl types.

Representative cross-linking agents include tetraallyloxyethane, divinylbenzene, divinyloctanedioate, divinyldodecanedioate, and divinyloctadecanedioate.

The copolymers employed in the present invention are, for the most part, known and have a molecular weight between about 2,000 and 500,000 and preferably between 4,000 and 200,000.

Representative copolymers usefully employed in the fatty composition according to the invention, include the following: vinyl acetate/allyl stearate, vinyl acetate/vinyl laurate, vinyl acetate/vinyl stearate, vinyl acetate/octadecene, vinyl acetate/octadecylvinylether, vinyl propionate/allyl laurate, vinyl propionate/vinyl laurate, vinyl stearate/1-octadecene, vinyl acetate/1-dodecene, vinyl stearate/ethylvinylether, vinyl propionate/cetylvinylether, vinyl stearate/allyl acetate, vinyl-2,2-dimethyloctanoate/vinyl laurate, allyl-2,2-dimethylpentanoate/vinyl laurate, vinyl dimethylpropionate/vinyl stearate, allyldimethylpropionate/vinyl stearate, vinyl propionate/vinyl stearate cross-linked with 0.2% of divinylbenzene, vinyldimethylpropionate/vinyl laurate cross-linked with 0.2% of divinylbenzene, vinyl acetate/octadecylvinylether cross-linked with 0.2% of tetraallyloxyethane, vinyl acetate/allyl stearate cross-linked with 0.2% of divinylbenzene, vinyl acetate/1-octadecene cross-linked with 0.2% of divinylbenzene and allyl propionate/allyl stearate cross-linked with 0.2% divinylbenzene.

The copolymers cross-linked or not, usefully employed in the present invention can be obtained according to conventional methods, i.e. by polymerization in mass, in suspension, in solution or in emulsion.

Preferably the polymerization is effected in solution in an organic solvent or in suspension in water.

As catalysts, one can use, for example benzoyl peroxide, lauroyl peroxide, or azobisisobutyronitrile.

The temperature of polymerization is generally between 50° to 130°C.

The present invention also has for an object cosmetic compositions, solid or semi-solid, containing as the fatty composition, the composition such as defined above.

According to the invention, the amount of fatty composition in the cosmetic composition, is generally between about 99.5 to 15% by weight with respect to the total weight of the cosmetic composition, it being understood that the amount of the copolymer relative to the total weight of the cosmetic composition cannot be lower than 1.5% by weight thereof.

The compositions according to the invention can be present either in the form of a lip rouge in stick or in paste form or in the form of a mascara.

When the compositions according to the invention are present in the form of sticks, they can be either lip rouges, or lip polishes. The difference between these two forms of the invention resides in the fact that the lip polishes do not contain or contain only a very small amount of dyes which serve only to tint the stick but which do not permit it to impart to the lips any significant amount of coloration.

In this particular form of the invention the fatty composition is preferably present in an amount between 75 to 99.5% with respect to the total weight of the stick.

The various components which can be introduced into these sticks are those conventionally used for this type of formulation. Among those one can mention, in particular, are dyes, soluble or insoluble, which are generally present in an amount between about 6 to 15%, solvents for certain dyes insoluble in the fatty body, and particularly eoisne derivatives, pearlescent agents in an amount of 2 to 20%, perfumes, anti-solar agents, antioxidants and perservatives.

Among the different dyes for lip rouges, one can mention in particular: the eosines and other halogenated derivatives of fluorescein (bromo-acids) and principally those known under the name of D and C Red No. 21, D and C Red No. 27, D and C Orange No. 5, inorganic pigments such as the oxides of iron, chromium, ultramarines (polysulfides of amino silicates) titanium dioxide, these compounds being employed in amounts of about 1 to 6%, organic pigments such as: D and C Red No. 36 and D and C Orange No. 17.

Finally in the list of dyes one can also include lakes such as the calcium lakes of D and C Red Nos. 7, 21 and 27, barium lakes of D and C Red Nos. 6 and 9, aluminum lakes of D and C Red No. 21 and D and C Yellow Nos. 5 and 6, and the zirconium lakes of D and C Red No. 21 and of D and C Orange No. 5.

Among the solvents for the dyes insoluble in the oils, one can mention glycols, esters of tetrahydrofurfuryl, polyethyleneglycols and monoalkanolamides.

Among the pearlescent agents one can mention particularly: bismuth oxychloride, mica-titanium and the crystals of guanine.

Among the antioxidant agents, one can mention particularly those of the phenolic type such as the propyl, octyl and dodecyl esters of gallic acid, butylated hydroxy anisole, butylated hydroxy toluene and nordihydroguaiaretic acid.

When the compositions are present in the form of pastes, they can also be lip rouges or lip polishes and contain then the same ingredients as the sticks. In this form of the invention, the fatty composition is also present in amounts essentially identical to that of the sticks.

However, in this latter case, the amount of wax is considerably lower and it is recommended preferably not to exceed 85% wax with respect to the total weight of the fatty composition.

These compositions which are in the form of sticks or pastes are preferably anhydrous although in certain cases they can contain certain quantities of water not exceeding generally 8 to 10% with respect to the total weight of the cosmetic composition.

When the cosmetic compositions according to the invention are present in the form of mascara, they are in a semi-solid form and can be either anhydrous or aqueous.

In this particular form of the invention, the amount of the fatty composition is preferably between 15 to 40% with respect to the total weight of the mascara.

When the mascara is anhydrous it contains in addition to the fatty composition a volatile component in an amount generally between about 35 to 50% with respect to the total weight of the mascara. Among the volatile components one can mention in particular are isoparaffin, oil of turpentine, isopropyl alcohol, ethyl alcohol, white spirits and the like.

When to the contrary the mascara is aqueous in form (generally in the form of an oil-in-water emulsion) it contains preferably from 50 to 70% by weight of water with respect to the total weight of the mascara, from 8 to 20% of an emulsifying agent such as the oleostearate of amino propanediol, the stearate or oleate of amino propanediol, of morpholine, or mono-, di- or triethanolamine, of mono-, di or tri-isopropanolamine, polyoxyethylenated fatty ethers or esters, or polyglycerols of fatty ethers or esters, etc. and a substance to improve the adherence and the drawing of the mascara, such as for example, derivatives of cellulose including hydroxy cellulose or even of gum arabic.

The mascaras which are either anhydrous or aqueous also contain dyeing agents and in particular certain pigments such as carbon black or black iron oxide, chromium oxides, yellow and red iron oxides and additionally certain metallic powders such as those of silver or aluminum.

The mascaras according to the invention can also contain other components conventionally employed such as perfumes, antioxidants and preservatives.

As has been indicated above the compositions which are present in the form of sticks, pastes or mascaras must not contain a quantity of copolymer lower than 1.5% by weight relative to the total weight of these types of compositions.

In that which concerns the maximum concentration of the copolymers in the cosmetic compositions, this is generally a function of the relative amounts of the fatty composition and is about 35% and preferably about 25% for sticks and pastes and about 15%, preferably about 10% for the mascara.

The following examples are given to illustrate the invention.

EXAMPLES OF PREPARING COPOLYMERS

Example 1

60% vinyl acetate/40% allyl stearate (molar ratio of 85% vinyl acetate/15% allyl stearate).

Into a one liter round bottomed flask provided with a mechanical agitator, nitrogen lead-in tube and a condenser, there are introduced 60 grams of vinyl acetate, 40 grams of allyl stearate and 3.4 grams of benzoyl peroxide in solution in 100 grams of toluene. The solution is heated with agitation for 18 hours at 100°C. After distillation of 75 grams of toluene under reduced pressure, 120 grams of methanol previously heated to 50°C are introduced therein. Vinyl methanol acetate azeotrope (boiling point equal 63.8°C) is distilled up to the recovery of about 100 grams of the mixture and then 120 grams of methanol heated to 50°C are again introduced. About 120 grams of the mixture are again distilled off. Then there are added 500 grams of methanol and the mixture is heated with agitation for 10 minutes at the boiling point of methanol. The polymer passes into solution which remains cloudy. The reaction mixture is then left to cool with agitation at 20°C and the polymer precipitates in the form of a paste. The remaining methanol is removed and the polymer is reprecipitated with methanol. After the elimination of the methanol, 400 grams of ethanol are introduced and the resulting mixture is heated with agitation for 10 minutes at the boiling point of ethanol. Thereafter the mixture is permitted to cool to 20°C with agitation. After removal of the ethanol containing the allyl stearate which has not reacted, the polymer is reprecipitated a last time with methanol. The polymer which precipitates is isolated and dried under reduced pressure without heating.
Yield: 40%
Viscosity: 0.83 cp $\overline{M}_n$ = 10,000.

Example 2

Preparation of 35% vinyl acetate/65% allyl stearate (molar ratio of vinyl acetate 67%/allyl stearate 33%).

Into a 500 milliliter round bottomed flask provided with a condenser, a nitrogen lead-in tube and an agitation means, there are introduced 35 grams of vinyl acetate, 65 grams of allyl stearate and 3.4 grams of benzoyl peroxide in solution in 100 grams of benzene. The solution is heated to reflux, with agitation for 19 hours. Then 3.4 grams of benzoyl peroxide in solution in 10 grams of benzene are introduced therein and the polymerization is continued for 14 additional hours. Finally 1.7 grams of benzoyl peroxide in solution in 5 grams of benzene are introduced in the reaction mixture and the polymerization is continued for 9 hours. The mixture is then left to cool, after which the solution is dumped into two liters of methanol. The polymer precipitates in the form of a white powder which is dried at 50°C under reduced pressure.
Yield: 96%
Viscosity: 1.10 cp.

Examples 3 to 23

By operating in a similar manner other copolymers have been obtained. These are listed in Table A below.

EXAMPLES OF PREPARATION - TABLE A

| Example | Copolymer prepared | Mole % | Weight % | Solvent | Nature and % of catalyst | Precipitating agent (b) | Viscosity (cp) (a) |
|---|---|---|---|---|---|---|---|
| 3 | Vinyl acetate<br>Vinyl laurate | 53<br>47 | 30<br>70 | Isopropanol | AIBN 2%<br>(c) | methanol | 0.81 |
| 4 | Vinyl acetate<br>Vinyl stearate | 70<br>30 | 40<br>60 | Methanol | AIBN 1% | Methanol | 1.95 |
| 5 | Vinyl propionate<br>Vinyl laurate | 43<br>57 | 25<br>75 | Isopropanol | AIBN 3% | Methanol | 0.74 |
| 6 | Vinyl stearate<br>1-octadecene | 77<br>23 | 80<br>20 | Isopropanol | AIBN 3% | Octane | 0.70 |
| 7 | Vinyl acetate<br>Dodecene | 66<br>34 | 50<br>50 | Isopropanol | AIBN 2% | Evaporate to dryness | 0.70 |
| 8 | Vinyl acetate<br>1-octadecene | 81<br>19 | 60<br>40 | Isopropanol | AIBN 2% | Water | 0.76 |
| 9 | Vinyl stearate<br>Ethyl vinyl ether | 50<br>50 | 80<br>20 | Methanol | AIBN 3% | Evaporate to dryness | 1.10 |
| 10 | Vinyl propionate<br>Cetyl vinyl ether | 94<br>6 | 85<br>15 | Isopropanol | AIBN 2% | Water | 0.79 |
| 11 | Vinyl acetate<br>Octadecyl vinyl ether | 77<br>23 | 50<br>50 | Isopropanol | AIBN 3% | Water | 0.70 |
| 12 | Vinyl propionate<br>Allyl laurate | 90<br>10 | 80<br>20 | Methanol | AIBN 3% | Water | 1.11 |
| 13 | Vinyl stearate<br>Allyl acetate | 53<br>47 | 80<br>20 | Methanol | AIBN 4% | Methanol | 0.89 |
| 14 | Vinyl-2,2-dimethyl octanoate<br>Vinyl laurate | 72<br>28 | 70<br>30 | Methanol | AIBN 4% | Methanol | 1.01 |
| 15 | Allyl-2,2-dimethyl pentanoate<br>Vinyl laurate | 25<br>75 | 20<br>80 | Methanol | AIBN 3% | Methanol | 0.69 |
| 16 | Vinyl dimethyl propionate<br>Vinyl stearate | 38<br>62 | 20<br>80 | Methanol | AIBN 1% | Methanol | 1.27 |
| 17 | Allyl dimethyl propanoate<br>Vinyl stearate | 48<br>52 | 30<br>70 | Methanol | AIBN 4% | Methanol | 0.70 |
| 18 | Vinyl propionate<br>Vinyl stearate cross-linked | 57 | 30 | Acetone | AIBN 3% | Evaporation to dryness | 0.97 |

EXAMPLES OF PREPARATION - TABLE A-continued

| Example | Copolymer prepared | Mole % | Weight % | Solvent | Nature and % of catalyst | Precipitating agent (b) | Viscosity (cp) (a) |
|---|---|---|---|---|---|---|---|
| 19 | with 0.2% of divinylbenzene<br>Vinyl dimethyl propanoate<br>Vinyl laurate cross-linked<br>with 0.2% of divinylbenzene | 43<br>24<br>76 | 70<br>15<br>85 | Isopropanol | AIBN 2% | Methanol | 0.76 |
| 20 | Vinyl acetate<br>Octadecyl vinyl ether cross-linked with 0.2% of tetra-allyloxyethane | 77<br>23 | 50<br>50 | Benzene | AIBN 3% | Ethanol | 0.61 |
| 21 | Vinyl acetate<br>Allyl stearate cross-linked<br>with 0.2% of divinylbenzene | 62<br>38 | 30<br>70 | Isopropanol | AIBN 2% | Methanol | 0.68 |
| 22 | Vinyl acetate<br>1-octadecene cross-linked<br>with 0.2% of divinylbenzene | 75<br>25 | 50<br>50 | Isopropanol | AIBN 2% | Evaporation to dryness | 0.6 |
| 23 | Allyl propionate<br>Vinyl stearate cross-linked<br>with 0.2% of divinylbenzene | 23<br>77 | 10<br>90 | Acetone | AIBN 2% | Evaporation to dryness | 0.74 |

Remarks: All the copolymers of Examples 3–23 have been prepared by heating in solution at 80°C for 24 hours.
(a) The viscosities have been measured in a 5% solution in toluene at 34.6°C.
(b) After the termination of the polymerization reaction, the mixture is poured into one of the solvents indicated above to precipitate the copolymer.
(c) AIBN = azobisisobutyronitrile.

EXAMPLES OF COMPOSITIONS ACCORDING TO THE INVENTION

Example I

One prepares in accordance with the invention a lip rouge in the form of a stick having the following composition:

| | | |
|---|---|---|
| Fatty composition A | 89.9 | grams |
| Butylated hydroxy toluene - antioxidant | 0.1 | g |
| Trimethyl-benzylidene-heptanone-anti-solar agent | 1 | g |
| Perfume | 1 | g |
| Dyes: | | |
| Titanium oxide | 4.5 | g |
| D and C Red No. 36 | 1 | g |
| Aluminum lake of F.D.C. Yellow 6 | 1 | g |
| Aluminum lake of D and C Red No. 27 | 1.5 | g |

Fatty composition A is an admixture of the following

| | | |
|---|---|---|
| Ozokerite | 16 | g |
| Lanolin | 28 | g |
| Oleyl alcohol | 10 | g |
| Cetyl ricinoleate | 20 | g |
| Triglycerides of octanoic acid | 20 | g |
| Oil of wheat germ | 1 | g |
| Copolymer according to Example 1 | 5 | g |

Example II

One prepares in accordance with the invention a pearlescent lip rouge in the form of a stick having the following composition:

| | | |
|---|---|---|
| Fatty Composition B | 79.9 | g |
| Butylated hydroxy toluene - antioxidant | 0.1 | g |
| Trimethyl-benzylidene-heptanone-anti-solar agent | 1 | g |
| Dyes: | | |
| Titanium oxide | 1 | g |
| Aluminum lake of D and C Red No. 27 | 1.5 | g |
| Black iron oxide | 1 | g |
| Yellow iron oxide | 0.5 | g |
| Mica-titanium | 15 | g |

Fatty composition B is an admixture of the following components:

| | | |
|---|---|---|
| Candellila wax | 9 | g |
| Microcrystalline wax | 4 | g |
| Mineral oil | 13 | g |
| Cetyl ricinoleate | 15 | g |
| Lanolin | 15 | g |
| Lanolin - liquid | 25 | g |
| Isopropyl lanolate | 14 | g |
| Copolymer according to Example 3 | 5 | g |

Example III

One prepares according to the invention a transparent lip polish in the form of a stick having the following composition:

| | | |
|---|---|---|
| Fatty composition C | 96.9 | g |
| Butylated hydroxy anisole - antioxidant | 0.1 | g |
| Perfume | 1 | g |
| Dyes: | | |
| Zirconium lake of D and C Red No. 21 | 0.5 | g |
| D and C Red No. 36 | 1 | g |
| Aluminum lake o F. D. C. Yellow No. 5 | 0.5 | g |

Fatty composition C is an admixture of the following components:

| | | |
|---|---|---|
| Ozokerite | 12.5 | g |
| Carnauba wax | 2 | g |
| Candellila wax | 2 | g |
| Hydrogenated lanolin | 5 | g |
| Ricin oil | 38.5 | g |
| Oleyl alcohol | 15 | g |
| Isopropyl lanolate | 10 | g |
| Lanolin - liquid | 5 | g |
| Copolymer of Example 1 | 10 | g |

Example IV

One prepares in accordance with the invention a lip rouge in the form of a stick having the following composition:

| | | |
|---|---|---|
| Fatty composition D | 89.9 | g |
| Butylated hydroxy toluene - antioxidant | 0.1 | g |
| Trimethyl-benzylidene-heptanone-anti-solar agent | 1 | g |
| Perfume | 1 | g |
| Dyes: | | |
| Titanium oxide | 4.5 | g |
| D & C Red No. 36 | 1 | g |
| Aluminum lake of F.D.C. Yellow 6 | 1 | g |
| Aluminum lake of D and C Red No. 27 | 1.5 | g |

Fatty composition D is identical to fatty composition C except that the 10 grams of the copolymer of Example 1 are replaced by the following mixture:

| | | |
|---|---|---|
| Copolymer according to Example 2 | 6 | g |
| Polyvinylstearate | 4 | g |

Example V

One prepares according to the invention a lip rouge in the form of a stick having the following composition:

| | | |
|---|---|---|
| Fatty composition E | 89.8 | g |
| Butylated hydroxy toluene - antioxidant | 0.1 | g |
| Trimethyl-benzylidene-heptanone-anti-solar agent | 1 | g |
| Perfume | 1 | g |
| Dyes: | | |
| Titanium oxide | 2.2 | g |
| Aluminum lake of D and C Red No. 27 | 3.6 | g |
| Black iron oxide | 0.4 | g |
| D and C Red No. 36 | 0.9 | g |
| Aluminum lake of D & C Yellow No. 6 | 1 | g |

Fatty composition E is an admixture of the following components:

| | | |
|---|---|---|
| Microcrystalline wax | 9 | g |
| Lanolin | 30 | g |
| Oleyl alcohol | 9 | g |
| Cetyl ricinoleate | 20 | g |
| Triglycerides of octanoic acid | 16 | g |
| Isopropyl lanolate | 10 | g |
| Oil of wheat germ | 1 | g |
| Copolymer of Example 4 | 5 | g |

In fatty composition E the copolymer according to Example 4 can advantageously be replaced by the same quantity of one of the copolymers prepared according to Examples 5, 6, 7 or 9.

Example VI

One prepares according to the invention a lip rouge in the form of a stick having the following composition:

| | | |
|---|---|---|
| Fatty Composition E' | 82.5 | g |
| Butylated hydroxy toluene - antioxidant | 0.1 | g |
| Perfume | 1 | g |
| Dyes: | | |
| Titanium oxide | 1.8 | g |
| D and C Orange No. 5 | 0.3 | g |
| Aluminum lake of D and C Yellow No. 6 | 8.8 | g |
| D and C Red No. 6 | 5.5 | g |

Fatty composition E' is identical to fatty composition E except that the 5 grams of the copolymer according to Example 4 have been replaced by the same quantity of the copolymer according to Example 10.

Example VII

One prepares in accordance with the invention a pearlescent lip rouge in the form of a stick having the following composition:

| | | |
|---|---|---|
| Fatty composition E'' | 78.85 | g |
| Butylated hydroxy toluene - antioxidant | 0.1 | g |
| Perfume | 1 | g |
| Dyes: | | |
| Zirconium lake of D and C Red. No. 21 | 0.8 | g |
| Black iron oxide | 0.05 | g |
| D and C Orange No. 5 | 0.2 | g |
| D and C Red No. 36 | 0.8 | g |
| Aluminum lake of D and C Yellow No. 6 | 3.2 | g |
| Mica-titanium | 15 | g |

Fatty composition E'' is identical to fatty composition E except that the 5 grams of copolymer according to Example 4 have been replaced by the same quantity of the copolymer according to Example 11.

Example VIII

One prepares according to the invention a lip rouge in the form of a stick having the following composition:

| | | |
|---|---|---|
| Fatty composition F | 89.62 | g |
| Butylated hydroxy toluene - antioxidant | 0.1 | g |
| Perfume | 1 | g |
| Dyes: | | |
| D and C Red No. 30 | 5 | g |
| Calcium lake of D and C Red No. 7 | 0.8 | g |
| D and C Red No. 36 | 0.5 | g |
| Titanium oxide | 2.6 | g |
| Black iron oxide | 0.38 | g |

Fatty composition F is an admixture of the following components:

| | | |
|---|---|---|
| Ozokerite | 13 | g |
| Lanolin - liquid | 8 | g |
| Oleyl alcohol | 15 | g |
| Carnauba wax | 3 | g |
| Ricin oil | 44 | g |
| Isopropyl lanolate | 12 | g |
| Copolymer of Example 20 | 5 | g |

Example IX

One prepares in accordance with the invention a lip polish in the form of a paste having the following composition:

| | | |
|---|---|---|
| Fatty composition G | 97.9 | g |
| Butylated hydroxy toluene - antioxidant | 0.1 | g |
| Perfume | 1 | g |
| Dyes: | | |
| Titanium oxide | 0.2 | g |
| Zirconium lake of D and C Red No. 21 | 0.3 | g |
| Aluminum lake of F.D.C. Yellow No. 6 | 0.2 | g |
| D and C Red No. 36 | 0.3 | g |

Fatty composition G is an admixture of the following components:

| | | |
|---|---|---|
| Lanolin | 30 | g |
| Lanolin-liquid | 30 | g |
| Vaseline | 10 | g |
| Mineral oil | 9 | g |
| Microcrystalline wax | 1 | g |
| Copolymer of Example 17 | 20 | g |

In this fatty composition G the copolymer according to Example 17 can advantageously be replaced by a copolymer prepared according to Examples 19 and 22.

Example X

One prepares in accordance with the invention a pearlescent lip polish in the form of a paste having the following composition:

| | | |
|---|---|---|
| Fatty Composition H | 80.9 | g |
| Butylated hydroxy anisole - antioxidant | 0.1 | g |
| Perfume | 1 | g |
| Dyes: | | |
| Aluminum lake of D and C Red No. 27 | 0.5 | g |
| D and C Red No. 36 | 0.5 | g |
| Aluminum Lake of F.D.C. Yellow No. 5 | 0.5 | g |
| Bismuth oxychloride | 16.5 | g |

Fatty composition H is an admixture of the following

| | | |
|---|---|---|
| Lanolin | 30 | g |
| Lanolin wax | 4 | g |
| Oleyl alcohol | 13 | g |
| Cetyl ricinoleate | 10 | g |
| Mineral oil | 3 | g |
| Ricin oil | 20 | g |
| Copolymer of Example 13 | 20 | g |

In fatty composition H the copolymer according to Example 13 can advantageously be replaced by the same quantity of a copolymer prepared according to Examples 12, 15 and 16.

Example XI

One prepares in accordance with the invention a lip polish in the form of a paste having the following composition:

| | | |
|---|---|---|
| Fatty composition I | 97.04 | g |
| Butylated hydroxy toluene - antioxidant | 0.1 | g |
| Perfume | 1 | g |
| Dyes: | | |
| Zirconium lake of D and C Red No. 21 | 0.4 | g |
| Calcium lake of D and C Red No. 7 | 0.12 | g |
| Black iron oxide | 0.14 | g |
| Aluminum lake of D and C Yellow No. 6 | 1.2 | g |

Fatty composition I is an admixture of the following components:

| | | |
|---|---|---|
| Microcrystalline wax | 1.5 | g |
| Ozokerite | 2.5 | g |
| Lanolin | 15 | g |
| Mineral oil | 37 | g |
| Bentonite - cationic | 4 | g |
| Copolymer of Example 23 | 10 | g |

Example XII

One prepares in accordance with the invention a slightly pearlescent lip polish in the form of a paste having the following composition:

| | | |
|---|---|---|
| Fatty composition J | 93.95 | g |
| Butylated hydroxy toluene - antioxidant | 0.1 | g |
| Perfume | 1 | g |
| Dye: | | |
| Zirconium lake of D and C Red No. 21 | 0.2 | g |
| D and C Red No. 21 | 0.05 | g |
| Calcium lake of D and C Red No. 7 | 0.2 | g |
| Aluminum lake of D and C Yellow No. 6 | 0.5 | g |
| Mica-titanium | 4 | g |

Fatty composition J is an admixture of the following components:

| | | |
|---|---|---|
| Microcrystalline wax | 2.5 | g |
| Ozokerite | 3 | g |
| Lanolin - liquid | 28 | g |
| Mineral oil | 11 | g |
| Lanolin | 23 | g |
| Solidified mineral oil | 15 | g |
| Bentonite - cationic | 7.5 | g |
| Copolymer of Example 18 | 10 | g |

In this fatty composition the copolymer according to Example 18 can advantageously be replaced by the same quantity of the copolymer prepared according to Examples 14, 20 or 21.

Example XIII

One prepares in accordance with the invention a lip polish in the form of a paste having the following composition:

| | | |
|---|---|---|
| Fatty composition K | 97.570 | g |
| Butylated hydroxy toluene - antioxidant | 0.1 | g |
| Perfume | 1 | g |
| Dyes: | | |
| Black iron oxide | 0.035 | g |
| D and C Red No. 6 | 0.37 | g |
| D and C Red No. 36 | 0.175 | g |
| Yellow iron oxide | 0.75 | g |

Fatty composition K is an admixture of the following components:

| | | |
|---|---|---|
| Microcrystalline wax | 1.5 | g |
| Ozokerite | 2 | g |
| Lanolin - liquid | 28 | g |
| Mineral oil | 11 | g |
| Lanolin | 20 | g |
| Solidified mineral oil | 15 | g |
| Bentonite - cationic | 7.5 | g |
| Copolymer according to Example 17 | 15 | g |

In fatty composition K the copolymer according to Example 17 can be replaced by mixture of copolymers prepared according to Examples 8 and 11 (10 grams of copolymer according to Example 8 and 5 grams of the copolymer according to Example 11).

Example XIV

One prepares according to the invention a lip rouge in the form of a paste having the following composition:

| | | |
|---|---|---|
| Fatty composition L | 85.9 | g |
| Butylated hydroxy toluene - antioxidant | 0.1 | g |
| Bentonite - cationic | 5 | g |
| Perfume | 1 | g |
| Dye: | | |
| Titanium oxide | 1 | g |
| Aluminum lake of D and C Red No. 27 | 3 | g |
| Calcium lake of D and C Red No. 7 | 4 | g |

Fatty composition L is an admixture of the following components:

| | | |
|---|---|---|
| Lanolin | 18 | g |
| Isopropyl lanolate | 18 | g |
| Mineral oil | 4 | g |
| Oleyl alcohol | 10 | g |
| Hydrogenated lanolin | 8 | g |
| Cetyl ricinoleate | 8 | g |
| Ricin oil | 18 | g |
| Copolymer of Example 1 | 20 | g |

Example XV

One prepares in accordance with the invention a lip rouge in the form of a paste having the following composition:

| | | |
|---|---|---|
| Fatty compolisition M | 83.9 | g |
| Butylated hydroxy anisole - antioxidant | 0.1 | g |
| Perfume | 1 | g |
| Bentonite - cationic | 3 | g |
| Dyes: | | |
| Titanium oxide | 1 | g |
| Aluminum lake of D and C Red No. 27 | 3 | g |
| D and C Red No. 30 | 3 | g |
| Calcium lake of D and C Red No. 7 | 5 | g |

Fatty composition M is identical to fatty composition G except that 20 grams of the copolymer of the latter are replaced by a mixture of:

| | | |
|---|---|---|
| Copolymer of Example 1 | 10 | g |
| Copolymer of Example 6 | 5 | g |
| Polyvinylstearate cross-linked with the aid of divinylbenzene | 5 | g |

Example XVI

One prepares according to the invention a lip rouge in the form of a paste having the following composition:

| | | |
|---|---|---|
| Fatty composition N | 76.9 | g |
| Butylated hydroxy toluene - antioxidant | 0.1 | g |
| Perfume | 1 | g |
| Bentonite - cationic | 4 | g |
| Dyes: | | |
| Calcium lake of D and C Red No. 7 | 1.5 | g |
| D and C Red No. 30 | 3 | g |
| Aluminum lake of F.D.C. Red No. 5 | 1.5 | g |
| Mica-titanium | 12 | g |

Fatty composition N is an admixture of the following components:

| | | |
|---|---|---|
| Microcrystalline wax | 1 | g |
| Candellila wax | 2 | g |
| Lanolin wax | 5 | g |
| Ricin oil | 8 | g |
| Cetyl ricinoleate | 8 | g |
| Mineral oil | 20 | g |
| Isopropyl lanolate | 11 | g |
| Triglycerides of decanoic acid | 15 | g |
| Copolymer of Example 21 | 30 | g |

In this fatty composition the copolymer according to Example 21 can advantageously be replaced by the copolymer according to Example 23.

Example XVII

One prepares in accordance with the invention a mascara having the following composition:

| | | |
|---|---|---|
| Fatty composition O | 18 | g |
| Oleostearate of aminopropanediol | 12 | g |
| Hydroxyethylcellulose | 1 | g |
| Demineralized water | 58.8 | g |
| Black iron oxide | 10 | g |
| Methyl para-hydroxy benzoate | 0.2 | g |

Fatty composition O is an admixture of the following components:

| | | |
|---|---|---|
| Carnauba wax | 99 | g |
| Copolymer of Example 1 | 11 | g |

Example XVIII

One prepares in accordance with the invention a mascara having the following composition:

| | | |
|---|---|---|
| Fatty composition P | 18 | g |
| Oleostearate of aminopropanediol | 12 | g |
| Hydroxyethylcellulose | 1 | g |
| Demineralized water | 58.8 | g |
| Yellow iron oxide | 6 | g |
| Black iron oxide | 4 | g |
| Methyl para-hydroxy benzoate | 0.2 | g |

Fatty composition P is an admixture of the following components:

| | | |
|---|---|---|
| Carnauba wax | 89 | g |
| Copolymer of Example 2 | 11 | g |

In this fatty composition the copolymer of Example 2 can advantageously be replaced by the same quantity of a copolymer according to Examples 3, 5, 7, 8 and 18.

Example XIX

One prepares in accordance with the invention a mascara having the following composition:

| | | |
|---|---|---|
| Fatty composition Q | 18 | g |
| Oleostearate of aminopropanediol | 12 | g |
| Hydroxyethylcellulose | 1 | g |
| Demineralized water | 58.8 | g |
| Polysulfide of aminosilicate | 8 | g |
| Black iron oxide | 2 | g |
| Methyl para-hydroxy benzoate | 0.2 | g |

Fatty composition Q is an admixture of the following components:

| | | |
|---|---|---|
| Carnauba wax | 89 | g |
| Copolymer of Example 12 | 11 | g |

In this fatty composition the copolymer of Example 12 can advantageously be replaced by the same quantity of the copolymer prepared according to Examples 20, 21 and 23.

Example XX

One prepares according to the invention an anhydrous mascara by admixing the following components:

| | | |
|---|---|---|
| Fatty composition R | 39 | g |
| Isoparaffin | 56.8 | g |
| Black iron oxide | 4 | g |
| Methyl para-hydroxy benzoate | 0.2 | g |

Fatty composition R is an admixture of the following components:

| | | |
|---|---|---|
| Beeswax | 62.5 | g |
| Lanolin alcohol | 12.5 | g |
| Acetylated lanolin | 10 | g |
| Copolymer of Example 14 | 15 | g |

Example XXI

One prepares in accordance with the invention an anhydrous mascara by admixing the following components:

| | | |
|---|---|---|
| Fatty composition S | 39 | g |
| Isoparaffin | 56.8 | g |
| Black iron oxide | 4 | g |
| Methyl para-hydroxy benzoate | 0.2 | g |

Fatty composition S is an admixture of the following components:

| | | |
|---|---|---|
| Beeswax | 62.5 | g |
| Lanolin alcohol | 12.5 | g |
| Acetylated lanolin | 10 | g |
| Copolymer of Example 9 | 15 | g |

In this fatty composition the copolymer of Example 9 can advantageously be replaced by an equal quantity of the copolymer prepared according to Examples 5, 6, 7, 15 and 19 or a mixture of these copolymers.

What is claimed is:

1. A fatty composition for use in producing a cosmetic composition selected from the group consisting of a lip rouge and a mascara, comprising a mixture of:
   i. at least one cosmetic fatty body consisting essentially of about 6–100% by weight of at least one cosmetic wax and 0–94% of at least one cosmetic oil, and
   ii. a non-toxic, fat soluble copolymer having the formula:

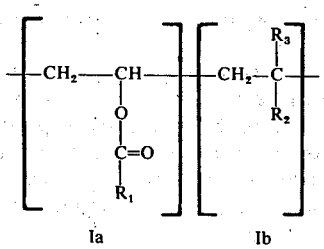

wherein:
$R_1$ represents a saturated hydrocarbon chain, linear or branched, having from 1 to 19 carbon atoms,
$R_2$ represents a member selected from the group consisting of
a.

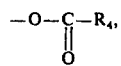

wherein $R_4$ has the same meaning as $R_1$ but is different from $R_1$ in the same copolymer,
b. —$CH_2$—$R_5$, wherein $R_5$ represents a saturated hydrocarbon chain, linear or branched, having from 5 to 25 carbon atoms,
c. —O—$R_6$, wherein $R_6$ represents a saturated hydrocarbon chain, having from 2 to 18 carbon atoms, and
d.

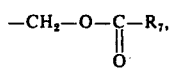

wherein $R_7$ represents a saturated hydrocarbon chain, linear or branched, having from 1 to 19 carbon atoms, and $R_3$ represents hydrogen when $R_2$ represents radicals (a), (b) or (c) or $R_3$ represents methyl when $R_2$ represents radical (d), the said copolymer including at least 15% by weight of at least one monomer of unit Ia or unit Ib, wherein said saturated hydrocarbon chain, linear or branched, has at least 7 carbon atoms, said copolymer having a molecular weight between 2,000 and 500,000 and being present in an amount of about 2–35% by weight relative to the total weight of the fatty composition.

2. The fatty composition according to claim 1 wherein said wax is selected from the group consisting of ozokerite, lanolin, lanolin alcohol, hydrogenated lanolin, acetylated lanolin, lanolin wax, beeswax, candellila wax, microcrystalline wax, carnauba wax, cetyl alcohol, stearyl alcohol, spermaceti, cocoa butter, a fatty acid of lanolin, petrolatum, a mono-, di- and triglyceride solid at 25°C, a fatty ester solid at 25°C, a silicone wax, stearyl monoethanolamide, rosin, glycol abietate, glycerol abietate, a hydrogenated oil solid at 25°C, a sucroglyceride and an oleate, myristate, lanolate, stearate and dihydroxystearate of calcium, magnesium, zirconium and aluminum.

3. The fatty composition according to claim 1, wherein said oil is selected from the group consisting of paraffin oil, perhydrosqualene, sweet almond oil, avocado oil, calophyllum oil, ricin oil, horse oil, hog oil, olive oil, a mineral oil having a boiling point between 310°–410°C, a silicone oil, linoleic alcohol, linolenic alcohol, oleyl alcohol, cereal germ oil, isopropyl lanolate, isopropyl palmitate, isopropyl myristate, butyl myristate, cetyl myristate, hexadecyl stearate, butyl stearate, decyl oleate, an acetyl glyceride, an octanoate and decanoate of glycol and glycerol, a ricinoleate of cetyl alcohol and isostearyl alcohol, isocetyl lanolate, isopropyl adipate, hexyl laurate and octyl dodecanol.

4. The fatty composition of claim 1, wherein said copolymer is crosslinked with a crosslinking agent selected from the group consisting of tetraallyloxyethane and divinylbenzene.

5. The composition according to claim 1 where, in the unit of formula Ib, $R_2$ represents

which is derived from a vinyl ester selected from the group consisting of vinyl acetate, vinyl propionate, vinyl butanoate, vinyl octanoate, vinyl decanoate, vinyl laurate, vinyl stearate, vinyl isostearate, vinyl-2,2-dimethyloctanoate, vinyl dimethylpropionate and vinyl cecanoate.

6. The composition according to claim 1 where, in the unit of formula Ib, $R_2$ represents the radical —$CH_2$—$R_5$ which is derived from an $\alpha$-olefin selected from the group consisting of 1-octene, 1-dodecene, 1-octadecene, 1-eicosene, and a mixture of $\alpha$-olefins having from 22 to 28 carbon atoms.

7. The composition according to claim 1 where, in the unit of formula Ib, $R_2$ represents the radical —O—$R_6$ which is derived from an alkylvinylether selected from the group consisting of ethylvinylether, n-butylvinylether, isobutylvinylether, decylvinylether, dodecylvinylether, cetylvinylether and octadecylvinylether.

8. The composition according to claim 1 where, in the unit of formula Ib, $R_2$ represents the radical

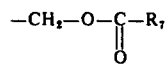

which is derived from an allyl or methallyl ester selected from the group consisting of allyl or methallyl acetate, propionate, dimethylpropionate, butyrate, hexanoate, octanoate, 2,2-dimethylpentanoate, decanoate, laurate, stearate and eicosanoate.

9. Composition according to claim 1 wherein said copolymer is constituted by 50 to 95 mole % of a unit of formula Ia and of 50 to 5 mole % of a unit of formula Ib, wherein $R_2$ represents a member selected from the group consisting of $-CH_2-R_5$, $-O-R_6$ and

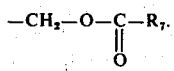

10. Composition according to claim 1 wherein said copolymer is constituted by 10 to 90 mole % of a unit of formula Ia and 90 to 10 mole % of a unit of formula Ib in which $R_2$ represents the radical

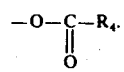

11. A cosmetic composition selected from the group consisting of a lip rouge and a mascara comprising the fatty composition of claim 1 in an amount between 99.5 and 15% by weight of the total weight of the cosmetic composition and a dye in an amount of 6–15 weight percent, the amount of said copolymer relative to the total weight of said cosmetic composition being at least 1.5% by weight.

12. The cosmetic composition of claim 11, wherein said fatty composition is present in an amount between 75 and 99.5% and the quantity of the wax in said fatty composition does not exceed 85% relative to the total weight of said fatty composition.

13. The cosmetic composition of claim 11, wherein water is also present in an amount not exceeding 8–10% relative to the total weight of said cosmetic composition.

14. The cosmetic composition of claim 11, wherein said fatty composition is present in an amount between 15 and 40% by weight and also contains water in an amount from 50–70% by weight of the total weight of said cosmetic composition.

15. The composition according to claim 11 which is anhydrous.

16. A lip polish comprising the fatty composition of claim 1 in an amount between 99.5 and 15% by weight of the total weight of the cosmetic composition, and an amount of dye from none to an amount sufficient to tint the lip polish, the amount of said copolymer relative to the total weight of said cosmetic composition being at least 1.5% by weight.

* * * * *